US010471136B2

(12) United States Patent
Tanaka et al.

(10) Patent No.: US 10,471,136 B2
(45) Date of Patent: Nov. 12, 2019

(54) PHARMACEUTICAL COMPOSITION FOR INJECTION

(71) Applicant: SUMITOMO DAINIPPON PHARMA CO., LTD., Osaka-shi, Osaka (JP)

(72) Inventors: Satoshi Tanaka, Ibaraki (JP); Tomomi Nakatani, Ibaraki (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 112 days.

(21) Appl. No.: 15/514,258

(22) PCT Filed: Sep. 26, 2015

(86) PCT No.: PCT/JP2015/077223
§ 371 (c)(1),
(2) Date: Mar. 24, 2017

(87) PCT Pub. No.: WO2016/047797
PCT Pub. Date: Mar. 31, 2016

(65) Prior Publication Data
US 2018/0344831 A1 Dec. 6, 2018

(30) Foreign Application Priority Data
Sep. 27, 2014 (JP) ................................ 2014-197667

(51) Int. Cl.
| A61K 38/10 | (2006.01) |
| A61K 39/00 | (2006.01) |
| A61K 47/12 | (2006.01) |
| A61K 47/20 | (2006.01) |
| A61K 47/26 | (2006.01) |
| A61K 9/00 | (2006.01) |
| C07K 7/08 | (2006.01) |

(52) U.S. Cl.
CPC .... *A61K 39/001153* (2018.08); *A61K 9/0019* (2013.01); *A61K 47/12* (2013.01); *A61K 47/20* (2013.01); *A61K 47/26* (2013.01); *C07K 7/08* (2013.01); *A61K 2039/572* (2013.01)

(58) Field of Classification Search
None
See application file for complete search history.

(56) References Cited

U.S. PATENT DOCUMENTS

| 5,496,718 A | 3/1996 | Hashimoto et al. |
| 9,181,302 B2 * | 11/2015 | Li ........................... A61K 39/00 |
| 9,539,299 B2 * | 1/2017 | Sugiyama ............ A61K 31/495 |
| 2004/0097703 A1 | 5/2004 | Sugiyama |
| 2005/0266014 A1 | 12/2005 | Sugiyama et al. |
| 2006/0166871 A1 | 7/2006 | Minamitake et al. |
| 2006/0217297 A1 | 9/2006 | Sugiyama et al. |
| 2007/0191271 A1 | 8/2007 | Mayhew et al. |
| 2010/0062010 A1 | 3/2010 | Nishihara et al. |
| 2010/0331262 A1 * | 12/2010 | Sugimura .......... A61K 39/0007 514/21.3 |
| 2011/0270212 A1 * | 11/2011 | Van Antwerp ..... A61K 31/7056 604/500 |
| 2012/0045465 A1 | 2/2012 | Sugiyama |
| 2014/0271693 A1 | 9/2014 | Nakatani et al. |
| 2015/0080321 A1 * | 3/2015 | Li .......................... A61K 39/00 514/21.4 |

FOREIGN PATENT DOCUMENTS

| JP | H06-135851 A | 5/1994 |
| JP | 2000-229882 A | 8/2000 |
| WO | WO 2000/006602 A1 | 2/2000 |
| WO | WO 2002/079253 A1 | 10/2002 |
| WO | WO 2003/097083 A1 | 11/2003 |
| WO | WO 2004/063217 A1 | 7/2004 |
| WO | WO 2007/063903 A1 | 6/2007 |
| WO | WO 2010/123065 A1 | 10/2010 |
| WO | WO 2014/142102 A1 | 9/2014 |
| WO | WO 2014/157692 A1 | 10/2014 |

OTHER PUBLICATIONS

Japan Pharmaceutical Excipients Council (editor), Iyakuhin Tenkabutsu Jiten, First Edition, p. 65 (1994).
Jain et al., "Trehalose and Protein Stability," *Current Protocols in Protein Science*, Supplement 59: 4.9.1-4.9.12 (2010).
Japanese Patent Office, International Search Report in International Patent Application No. PCT/JP2015/077223 (dated Dec. 22, 2015).

\* cited by examiner

*Primary Examiner* — Satyanarayana R Gudibande
(74) *Attorney, Agent, or Firm* — Leydig, Voit & Mayer, Ltd.

(57) ABSTRACT

The present invention provides an injectable pharmaceutical composition containing the following components:
(a) one or more kinds of peptides selected from a peptide represented by the formula (1):

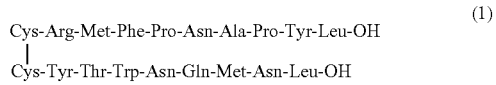

(1)

wherein the bond between Cys and Cys is a disulfide bond, Leu-OH shows that the C-terminal of Leu is a free carboxyl group, and other bond is a peptide bond, a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and salts thereof,
(b) trehalose or trehalose hydrate, and
(c) a pH adjuster.

22 Claims, 2 Drawing Sheets
Specification includes a Sequence Listing.

PHARMACEUTICAL COMPOSITION FOR INJECTION

CROSS-REFERENCE TO RELATED APPLICATIONS

This patent application is the U.S. national phase of International Patent Application No. PCT/JP2015/077223, filed Sep. 26, 2015, which claims the benefit of Japanese Patent Application No. 2014-197667, filed on Sep. 27, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 5,069 bytes ASCII (Text) file named "728353 SequenceListing.txt," created Mar. 24, 2017.

TECHNICAL FIELD

The present invention belongs to the field of cancer immunotherapy, and relates to an injectable pharmaceutical composition comprising WT1 protein-derived cancer antigen peptide having a cytotoxic T cell-inducing activity.

BACKGROUND ART

Generally, the WT1 protein-derived cancer antigen peptide is a partial peptide derived from human WT1 protein consisting of 449 amino acids (SEQ ID NO: 2), and is specifically a peptide consisting of 8-12 amino acids or a dimer thereof. It is presented to a major histocompatibility complex (MHC) class I antigen, and includes a peptide which is antigen-recognized by cytotoxic T cell (cytotoxic T-lymphocyte, hereinafter to be referred to as CTL). MHC in human is called human leukocyte antigen (HLA).

Among the WT1 protein-derived partial peptides, partial peptide consisting of the amino acid sequence shown by Arg-Met-Phe-Pro-Asn-Ala-Pro-Tyr-Leu (SEQ ID NO: 3) (WT1$_{126\text{-}134}$ peptide) and modified peptide obtained by modifying the second amino acid from the N terminus of partial peptide consisting of the amino acid sequence shown by Cys-Met-Thr-Trp-Asn-Gln-Met-Asn-Leu (SEQ ID NO: 6) (WT1$_{235\text{-}243}$ peptide) from methionine to tyrosine (i.e., peptide consisting of the amino acid sequence shown by Cys-Tyr-Thr-Trp-Asn-Gln-Met-Asn-Leu (SEQ ID NO: 5)) have been reported to be useful as peptides that bind to HLA to induce CTL (see patent documents 1-4). However, a modified peptide obtained by conjugating these two peptides via a disulfide bond between cysteine residues has not been known, and an optimal cancer vaccine composition therefor has neither been known.

On the other hand, among the WT1 protein-derived partial peptides, partial peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) (WT1$_{34\text{-}51}$ peptide) by itself is useful as a peptide that binds to HLA to induce CTL, and it has further been reported that combined use with the aforementioned peptide provides effects as helper peptide (see patent document 5). However, an optimal cancer vaccine composition containing this peptide has not been known.

Since an optimal cancer vaccine composition containing WT1$_{126\text{-}134}$ peptide and/or modified WT1$_{235\text{-}243}$ peptide, and WT1$_{34\text{-}51}$ peptide is useful as a cancer vaccine, the development of a formulation ensuring stability of these peptides has been expected.

DOCUMENT LIST

Patent Documents patent document 1: WO 00/06602
patent document 2: WO 02/079253
patent document 3: WO 2004/063217
patent document 4: WO 2007/063903
patent document 5: WO 2010/123065

SUMMARY OF THE INVENTION

Problems to be Solved by the Invention

A problem of the present invention is to provide a stable injectable pharmaceutical composition of a peptide represented by the formula (1) or WT1 partial peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1), which can be used for formulating a cancer vaccine formulation comprising the peptide:

wherein the bond between Cys and Cys shows a disulfide bond, Leu-OH shows that the C-terminal of Leu is a free carboxyl group, and other bond is a peptide bond.

Means of Solving the Problems

The present inventors have conducted intensive studies in an attempt to solve the above-mentioned problem and found that a liquid formulation containing a peptide represented by the formula (1) or WT1 partial peptide having the sequence shown in SEQ ID NO: 1, as well as trehalose and a pH adjuster, affords a liquid formulation and/or a freeze-dried formulation superior in formulation stability, which resulted in the completion of the present invention.

That is, the present invention relates to the following.
1. An injectable pharmaceutical composition comprising the following components:
(a) one or more kinds of peptides selected from a peptide represented by the formula (1):

wherein the bond between Cys and Cys is a disulfide bond, Leu-OH shows that the C-terminal of Leu is a free carboxyl group, and other bond is a peptide bond, a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and salts thereof,
(b) trehalose or trehalose hydrate, and
(c) a pH adjuster.

2. The composition of 1, wherein the component (a) is one or more kinds of peptides selected from a peptide represented by the formula (1) and a salt thereof.
3. The composition of 2, further comprising mannitol.
4. The composition of 3, wherein the mannitol is D-mannitol.
5. The composition of any one of 2-4, further comprising methionine.
6. The composition of 5, wherein the methionine is L-methionine.
7. The composition of any one of 2-6, which has a pH of 1-3.
8. The composition of any one of 2-7, which is a liquid formulation or a suspension formulation, wherein the content of component (b) is 1-100 mg/g.
9. The composition of any one of 3-8, which is a liquid formulation or a suspension formulation, wherein the content of mannitol is 1-50 mg/g.
10. The composition of any one of 5-9, which is a liquid formulation or a suspension formulation, wherein the content of methionine is 1-30 mg/g.
11. The composition of 1, wherein the component (a) is one or more kinds of peptides selected from a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and a salt thereof.
12. The composition of 11, further comprising a solubilizing agent.
13. The composition of 12, wherein the solubilizing agent is citric acid, lactic acid, tartaric acid, acetic acid, or trifluoroacetic acid.
14. The composition of 12, wherein the solubilizing agent is tartaric acid.
15. The composition of any one of 12-14, which has a pH of 2-3.
16. The composition of 11, which has a pH of 5-10.
17. The composition of any one of 11-16, which is a liquid formulation or a suspension formulation, wherein the content of component (b) is 1-100 mg/g.
18. The composition of any one of 12-15, which is a liquid formulation or a suspension formulation, wherein the content of the solubilizing agent is 0.1-10 mg/g.
19. The composition of any one of 11-18, wherein the acid used as the pH adjuster is a weak acid.
20. The composition of 1, wherein the component (a) comprises one or more kinds of peptides selected from a peptide represented by the formula (1) and a salt thereof, and one or more kinds of peptides selected from a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and a salt thereof.
21. The composition of 20, further comprising mannitol.
22. The composition of 20 or 21, further comprising methionine.
23. The composition of any one of 20-22, further comprising a solubilizing agent.
24. The composition of any one of 20-23, which has a pH of 2-3.
25. The composition of any one of 20-24, which is a liquid formulation or a suspension formulation, wherein the content of component (b) is 1-100 mg/g.
26. The composition of any one of 21-25, which is a liquid formulation or a suspension formulation, wherein the content of mannitol is 1-50 mg/g.
27. The composition of any one of 22-26, which is a liquid formulation or a suspension formulation, wherein the content of methionine is 1-30 mg/g.
28. The composition of any one of 23-27, which is a liquid formulation or a suspension formulation, wherein the content of the solubilizing agent is 0.1-10 mg/g.
29. A freeze-dried formulation obtained by freeze-drying the composition of any one of 8-10, 17, 18, and 25-28.
30. The composition of any one of 1-18, which is a liquid formulation, a suspension formulation, or a freeze-dried formulation.
31. The composition of any one of 1-7, 11-16, 19-24, and 30, which is a liquid formulation or a suspension formulation.
32. The composition of any one of 20-24, which is produced by adding a composition of any one of 11-15, which is in the form of a liquid formulation, to a composition of any one of 2-7, which is in the form of a freeze-dried formulation.
33. The composition of 32, which is a liquid formulation or a suspension formulation.
34. A cancer vaccine composition comprising a composition of any one of 1-28, and 30-33.
35. The composition of 34, further comprising an adjuvant.
36. The composition of 35, wherein the adjuvant is Montanide.
37. A method of improving stability of component (a) in an injectable pharmaceutical composition:
(a) one or more kinds of peptides selected from a peptide represented by the formula (1):

wherein the bond between Cys and Cys is a disulfide bond, Leu-OH shows that the C-terminal of Leu is a free carboxyl group, and other bond is a peptide bond, a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and salts thereof, which method comprising blending the above-mentioned component (a), as well as the following components (b) and (c):
(b) trehalose or trehalose hydrate
(c) a pH adjuster
in the composition.
38. A method of improving stability of peptide (a) in a cancer vaccine composition:
(a) one or more kinds of peptides selected from a peptide represented by the formula (1):

wherein the bond between Cys and Cys is a disulfide bond, Leu-OH shows that the C-terminal of Leu is a free carboxyl group, and other bond is a peptide bond, a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and salts thereof, which method comprising blending the above-mentioned component (a), as well as the following components (b), (c) and (d):
(b) trehalose or trehalose hydrate
(c) a pH adjuster
(d) methionine
in the composition.

39. The method of producing a composition of any one of 20-24, wherein a composition of any one of 11-15, which is in the form of a liquid formulation, is added to a composition of any one of 2-7, which is in the form of a freeze-dried formulation.

40. A method of producing a cancer vaccine composition, comprising adding a composition obtained by the method of 39 to an adjuvant.

41. The composition of 18, wherein the content of component (b) is 1-100 mg/g.

42. The composition of any one of 1-18, wherein the pH adjuster is hydrochloric acid and/or sodium hydroxide.

Effect of the Invention

Using the injectable pharmaceutical composition of the present invention, a cancer vaccine composition stably containing the peptide of the present invention having a cytotoxic T cell-inducing activity can be produced, and a cancer vaccine superior in the formulation stability can be prepared. In addition, when the injectable pharmaceutical composition is freeze-dried to give a freeze-dried formulation, a freeze-dried formulation stably maintaining peptide can be prepared.

BRIEF DESCRIPTION OF THE DRAWINGS

FIG. 1 is a graph showing the results of Experimental Example 4. The vertical axis shows the number of cells that reacted in the seeded cells number, and the horizontal axis shows peptide pulsed in vitro. In FIG. 1, the black bar shows the results of culture of HLA-A*02:01 transgenic mouse-derived splenocytes by pulsing the peptide shown in SEQ ID NO: 3, and the white bar shows the results of culture without pulsing.

FIG. 2 is a graph showing the results of Experimental Example 4. The vertical axis shows the number of cells that reacted in the seeded cells number, and the horizontal axis shows peptide pulsed in vitro. In FIG. 2, the black bar shows the results of culture of HLA-A*24:02 transgenic mouse-derived splenocytes by pulsing the peptide shown in SEQ ID NO: 5, and the white bar shows the results of culture without pulsing.

DESCRIPTION OF EMBODIMENTS

The embodiment of the present invention is explained in detail in the following.

In the present specification, a preferable embodiment of each exemplification may be combined with a preferable embodiment of other exemplification, or may be incorporated into the corresponding exemplification described in the aforementioned 1-42.

In the present invention, the "injectable pharmaceutical composition" refers to a composition containing the peptide of the present invention and one or more components other than the peptide. A cancer vaccine composition can be prepared by mixing an injectable pharmaceutical composition and various adjuvants.

The injectable pharmaceutical composition of the present invention can be provided in the form of a solution, a suspension, a freeze-dried formulation and the like.

In the present invention, the "liquid formulation" refers to respective components contained in the "injectable pharmaceutical composition", which are dissolved in a solvent. While water is generally used as the "solvent" in the present invention, a pharmacologically acceptable solvent such as propylene glycol, polyethylene glycol and the like can be partially mixed with water as long as the effect of the invention is not affected. Preferred is water. In addition, the below-mentioned "freeze-dried formulation" added to water and dissolved therein is also included in the "liquid formulation" of the present invention.

In the present invention, the "suspension formulation" is obtained by mixing respective components contained in the "injectable pharmaceutical composition" with a dispersing medium and suspending same therein. While water is generally used as the "dispersing medium" in the present invention, a pharmacologically acceptable solvent such as propylene glycol, polyethylene glycol and the like can be partially mixed with water as long as the effect of the invention is not affected. Preferred is water. In addition, the below-mentioned "freeze-dried formulation" added to water and suspended therein is also included in the "suspension formulation" of the present invention.

In the present invention, the "freeze-dried formulation" is obtained by freeze-drying the "liquid formulation" or "suspension formulation" in the present invention. Generally, it is performed to improve chemical or physical stability of peptide in the "liquid formulation" or "suspension formulation". When it is used as a cancer vaccine, a suitable amount of water is added, and the mixture is stirred to give a liquid formulation or a suspension formulation, which is mixed with various adjuvants to prepare a cancer vaccine composition.

In the present invention, the "peptide" is a cancer antigen peptide for preparing a cancer vaccine, and is a peptide selected from the group consisting of a peptide represented by the formula (1), and a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1), or a salt thereof.

(1)

wherein the bond between Cys and Cys is a disulfide bond, Leu-OH shows that the C-terminal of Leu is a free carboxyl group, and other bond is a peptide bond.

In the present specification, the peptide has the N-terminus on the left side, and each amino acid symbol means the following amino acid residue.

Ala or A: alanine residue
Arg or R: arginine residue
Asn or N: asparagine residue
Asp or D: aspartic acid residue
Cys or C: cysteine residue
Gln or Q: glutamine residue
Glu or E: glutamic acid residue
Gly or G: glycine residue
His or H: histidine residue
Ile or I: isoleucine residue
Leu or L: leucine residue
Lys or K: lysine residue
Met or M: methionine residue
Phe or F: phenylalanine residue
Pro or P: proline residue
Ser or S: serine residue
Thr or T: threonine residue Trp or W: tryptophan residue
Tyr or Y: tyrosine residue
Val or V: valine residue The "peptide represented by the formula (1)" refers to a peptide consisting of the amino acid sequence shown by Cys-Arg-Met-Phe-Pro-Asn-Ala-Pro-Tyr-Leu (SEQ ID NO: 4), wherein the cysteine residue is bonded to the N-terminal of Arg-Met-Phe-Pro-Asn-Ala-Pro-Tyr-Leu (SEQ ID NO: 3), and the cysteine residue of a peptide shown by Cys-Tyr-Thr-Trp-Asn-Gln-Met-Asn-Leu (SEQ ID NO: 5) are bonded to each other by a disulfide bond.

The peptide consisting of the amino acid sequence shown by Arg-Met-Phe-Pro-Asn-Ala-Pro-Tyr-Leu (SEQ ID NO: 3) is a partial peptide consisting of 9 continuous amino acids from the 126th arginine (Arg) to the 134th leucine (Leu) ($WT1_{126-134}$peptide) from the N-terminal of a protein (specifically, human WT1 protein consisting of 449 amino acids (SEQ ID NO: 2)), which is a gene product of a tumor suppressor gene WT1 for Wilms' tumor. This peptide is a peptide presented to MHC class I antigen and recognized as antigen by CTL.

The peptide consisting of the amino acid sequence shown by Cys-Tyr-Thr-Trp-Asn-Gln-Met-Asn-Leu (SEQ ID NO: 5) is a modified peptide which is a partial peptide consisting of 9 continuous amino acids from the 235th cysteine (Cys) to the 243rd leucine (Leu) ($WT1_{235-243}$ peptide) from the N terminal of the WT1 protein, wherein the second amino acid from the N terminal is modified from methionine (Met) to tyrosine (Tyr). This peptide is a peptide presented to MHC class I antigen and recognized as antigen by CTL.

The "peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1)" is a partial peptide consisting of 18 amino acids from the 34th tryptophan (Trp) to the 51st leucine (Leu) ($WT1_{34-51}$ peptide) from the N terminal of the WT1 protein. This peptide is a peptide presented to MHC class II antigen and induces WT1 specific helper T cell.

The salt of the peptide represented by the formula (1) or the peptide consisting of the amino acid sequence shown by SEQ ID NO: 1 is not particularly limited as long as it is a pharmaceutically acceptable salt. Examples of the "salt" in the present invention include acid addition salt and base addition salt. Examples of the acid addition salt include inorganic acid salts such as hydrochloride, hydrobromide, sulfate, hydroiodide, nitrate, phosphate and the like, and organic acid salts such as citrate, oxalate, acetate, formate, propionate, benzoate, trifluoroacetate, maleate, tartrate, methanesulfonate, benzenesulfonate, p-toluenesulfonate and the like. Examples of the base addition salt include salts with inorganic base such as sodium salt, potassium salt, calcium salt, magnesium salt, ammonium salt and the like, salts with organic base such as triethylammonium salt, triethanolammonium salt, pyridinium salt, diisopropylammonium salt etc., and the like, furthermore, amino acid salts of basic or acidic amino acids such as arginine, aspartic acid, glutamic acid and the like.

The peptide of the present invention also encompasses hydrates, solvates such as ethanol solvate and the like of a peptide represented by the formula (1) or a salt thereof, a peptide consisting of the amino acid sequence shown by SEQ ID No: 1 or a salt thereof. Furthermore, the peptide of the present invention encompasses any stereoisomers or a salt thereof such as any diastereomer, enantiomer and the like and any crystals in any embodiments, of the peptide represented by the formula (1), that can be present.

The peptide represented by the formula (1) or a salt thereof can be produced by the method described in the Examples in the present specification, or a known method (see patent documents 2-4 etc.). On the other hand, the peptide consisting of the amino acid sequence shown by SEQ ID NO: 1 or a salt thereof can be produced by a known method (see patent document 5). In addition, the peptide of the present invention can be produced by a method generally used in the pertinent technical field. Examples of the production method include the methods described in the documents (Peptide Synthesis, Interscience, New York, 1966; The Proteins, Vol. 2, Academic Press Inc., New York, 1976; peptide synthesis, Maruzen Co., LTD., 1975; Basics and Experiment of Peptide Synthesis, Maruzen Co., LTD., 1985; Development of Pharmaceutical Product subsequent vol. 14, Peptide Synthesis, Hirokawa Shoten, 1991) and the like.

When the peptide of the present invention obtained by the above-mentioned method is a free form, the free form can be converted to a suitable salt by a known method or a method analogous thereto. Conversely, when the peptide of the present invention is obtained as a salt, the salt can be converted to a free form or other salt by a known method or a method analogous thereto.

The injectable pharmaceutical composition of the present invention may contain a peptide represented by the formula (1) or one kind of salt thereof, each singly, or may contain the peptide and one or more kinds of salts thereof, or two or more kinds of salts of the peptide (hereinafter sometimes to be comprehensively referred to as "peptide (1)"). Similarly, the injectable pharmaceutical composition of the present invention may contain a peptide consisting of the amino acid sequence shown by SEQ ID NO: 1 or one kind of salt thereof, each singly, or may contain the peptide and one or more kinds of salts thereof, or two or more kinds of salts of the peptide (hereinafter sometimes to be comprehensively referred to as "peptide (2)"). Furthermore, the injectable pharmaceutical composition of the present invention optionally contains both peptide (1) and peptide (2).

When the injectable pharmaceutical composition of the present invention is a liquid formulation or a suspension formulation (hereinafter sometimes to be referred to as "the formulation in a liquid form of the present invention"), the content of the peptide of the present invention relative to the weight of the formulation in a liquid form of the present invention is not particularly defined, and it only needs to be pharmacologically acceptable or acceptable for property. Of the peptides of the present invention, for example, the content of peptide (1) (when two or more kinds of peptides are contained, the whole amount thereof) is preferably 0.5 mg-200 mg/g, further preferably 0.5 mg-100 mg/g, 0.5 mg-50 mg/g, or 1 mg-25 mg/g, which can be selected according to the object. On the other hand, the content of peptide (2) (when two or more kinds of peptides are contained, the whole amount thereof) is preferably 0.05 mg-200 mg/g, further preferably, 0.05 mg-100 mg/g, 0.05 mg-50 mg/g, or 0.1 mg-25 mg/g, which can be selected according to the object. When the liquid formulation of the present invention contains both peptide (1) and peptide (2), the weight ratio of peptide (1) and peptide (2) can be appropriately selected from the range of 1:0.1-1:5.

When the injectable pharmaceutical composition of the present invention is a freeze-dried formulation (hereinafter sometimes to be referred to as "the freeze-dried formulation of the present invention"), the content of the peptide of the present invention per volume is not particularly defined. The freeze-dried formulation of the present invention is obtained by freeze-drying the formulation in a liquid form of the present invention, and the content of the peptide only needs to satisfy the content of the formulation in a liquid form. A formulation in a liquid form of the present invention, which has a higher concentration than that before freeze-drying, can be obtained by dissolving or dispersing, in a smaller amount of water etc. than the liquid amount of the preparation in a liquid form of the formulation invention before freeze-drying, during water recovery of the freeze-dried formulation of the present invention.

The injectable pharmaceutical composition of the present invention characteristically contains, in addition to the above-mentioned peptide of the present invention (component (a)), the following components (b) and (c):
(b) trehalose or trehalose hydrate
(c) a pH adjuster.

In the present invention, "trehalose" is one kind of disaccharide formed by 1,1-glycosidic linkage of glucose. Trehalose may be anhydride or hydrate thereof. Preferred is trehalose hydrate. The injectable pharmaceutical composition of the present invention may contain trehalose in a single form of anhydride or hydrate thereof, or two or more kinds thereof may be contained in combination. In the injectable pharmaceutical composition of the present invention, the content of trehalose relative to the weight of the composition is not particularly defined. The content thereof relative to the weight of the formulation in a liquid form of the present invention (when contained in the form including two or more kinds, the whole amount thereof) is, for example, 1-50 mg/g, 1-70 mg/g, 1-100 mg/g, 1-150 mg/g, 1-200 mg/g, 3-50 mg/g, 3-70 mg/g, 3-100 mg/g, 3-150 mg/g, 3-200 mg/g, 5-50 mg/g, 5-70 mg/g, 5-100 mg/g, 5-150 mg/g, 5-200 mg/g or the like.

In the present invention, the "pH adjuster" is a pH adjuster generally used for pharmaceutical formulation. Specific examples thereof include inorganic acids such as hydrochloric acid, sulfuric acid, phosphoric acid, disodium phosphate, dibasic potassium phosphate, sodium dihydrogen phosphate, potassium dihydrogen phosphate, tribasic sodium phosphate and the like, or a salt thereof, organic acids such as nitric acid, acetic acid, citric acid, tartaric acid, lactic acid, maleic acid, sodium acetatehydrate, anhydrous sodium acetate, sodium citratehydrate, sodium dihydrogen citrate, sodium tartrate and the like, or a salt thereof, inorganic bases such as sodium hydroxide, potassium hydroxide, aqueous ammonia and the like, and organic bases such as tromethamol, histidine, L-arginine, meglumine and the like. Preferred are citric acid, lactic acid, tartaric acid, hydrochloric acid, sulfuric acid, nitric acid, sodium hydroxide and potassium hydroxide, trimethanol, histidine, L-arginine, and meglumine, and further preferred are tartaric acid, hydrochloric acid, and sodium hydroxide, tromethamol, L-arginine, and meglumine.

From another aspect, when component (a) is peptide (2), an acid as a pH adjuster is preferably a weak acid.

A pH adjuster is added to adjust the pH of the formulation in a liquid form of the present invention to fall within a pH range capable of ensuring the stability of the peptide of the present invention. Since the pH range capable of ensuring the stability of the peptide of the present invention varies depending on the kind of peptide contained in the formulation in a liquid form of the present invention as mentioned below, a pH adjuster suitable therefor is used.

When the injectable pharmaceutical composition of the present invention contains peptide (1) alone, the formulation in a liquid form of the present invention has a pH of 1-10. When the formulation in a liquid form is a liquid formulation, the pH is preferably 1-4, further preferably 1-3, most preferably 2-3, from the aspects of solubility and stability. When the formulation in a liquid form is a suspension formulation, pH 5-10 is preferable in view of solubility. In an embodiment other than those mentioned above, when the formulation in a liquid form is a liquid formulation, preferable pH includes 1.5-4.5, 1.5-3.5, 1.5-3.0, 2.0-3.0. For a suspension preparation, preferable pH includes 4-9, 4-6, 5-9.

On the other hand, when the injectable pharmaceutical composition of the present invention contains peptide (2) alone, the formulation in a liquid form of the present invention has pH 2-10, more specifically 2-3, 3-9, 6-9, 7. The pH is preferably 5-10, further preferably 6-8, from the aspect of stability.

Furthermore, when the injectable pharmaceutical composition of the present invention contains peptide (1) and peptide (2), the formulation in a liquid form of the present invention has a pH of 2-10. When the formulation in a liquid form is a liquid formulation, a preferable pH includes 2-4, 2-3, 1.7-3.2, and 1.5-3.5 from the aspect of stability.

In the present specification, numbers are rounded to one digit below the number being described. For example, when the number is 2, it shows not less than 1.5 and less than 2.5.

When the formulation in a liquid form of the present invention does not contain a pH adjuster and shows a higher pH value than the desired pH range, the pH can be adjusted to a desired one by adding an inorganic acid, an organic acid and the like as a pH adjuster. As the inorganic acid and organic acid, those mentioned above can be used.

When the formulation in a liquid form of the present invention does not contain a pH adjuster and shows a lower pH value than the desired pH range, an inorganic base or an organic base can be used as a pH adjuster. As the inorganic base and organic base, those mentioned above can be used. When the injectable pharmaceutical composition of the present invention contains peptide (2) alone, an inorganic base or an organic base is preferably used as a pH adjuster. Specifically, disodium hydrogen phosphate, tromethamol, histidine, L-arginine, and meglumine and the like can be mentioned. Preferred are disodium hydrogen phosphate, tromethamol, L-arginine, and meglumine. In the injectable pharmaceutical composition of the present invention, the content of organic base relative to the weight of the composition is not particularly defined. The content thereof relative to the weight of the formulation in a liquid form of the present invention is, for example, 1-100 mg/g, 1-50 mg/g, 1-150 mg/g, 5-100 mg/g, 5-50 mg/g, 5-150 mg/g, 10-100 mg/g, 10-50 mg/g, 10-150 mg/g or the like.

When the injectable pharmaceutical composition of the present invention contains peptide (1) as component (a), the composition may contain mannitol.

In the present invention, "mannitol" is one kind of sugar alcohol, classified into hexitol, and corresponds to a reduced form of mannose. Mannitol contains an optical isomer, including D form, L form and DL form, and use of any of these shows no influence on the effect of the present invention. Preferred is naturally occurring D-mannitol. While mannitol includes a plurality of crystal systems, use of any of them shows no influence on the effect of the present invention. In the injectable pharmaceutical composition of the present invention, the content of mannitol relative to the weight of the composition is not particularly defined. The content thereof relative to the weight of the formulation in a liquid form of the present invention is, for example, 1-20 mg/g, 1-30 mg/g, 1-50 mg/g, 3-20 mg/g, 3-30 mg/g, 5-20 mg/g, 5-30 mg/g or the like.

When the injectable pharmaceutical composition of the present invention contains peptide (2) as component (a), the composition preferably further contains a solubilizing agent to prevent the solubility of the peptide from becoming unstable. As the "solubilizing agent", an organic acid can be used. Using a solubilizing agent, peptide (2) can be rapidly dissolved in the dissolution step of the liquid preparation. Furthermore, for a freeze-dried formulation obtained by freeze-drying the formulation in a liquid form of the present invention, when the freeze-dried formulation is reconstituted using water for injection, it can be rapidly redissolved. Specific examples of the solubilizing agent include citric acid, lactic acid, tartaric acid, acetic acid, and trifluoroacetic acid and the like. Preferred are citric acid, lactic acid, and tartaric acid, and further preferred is tartaric acid. In the injectable pharmaceutical composition of the present invention, the content of the solubilizing agent relative to the weight of the composition is not particularly defined. The content thereof relative to the weight of the formulation in a liquid form of the present invention is, for example, 1-5 mg/g, 1-10 mg/g, 1-15 mg/g, 1-20 mg/g, 3-10 mg/g, 3-15 mg/g, 3-20 mg/g, 5-10 mg/g, 5-15 mg/g, 5-20 mg/g, 0.1-5 mg/g, 0.1-10 mg/g, 0.1-15 mg/g, 0.1-20 mg/g, 0.3-10 mg/g, 0.3-15 mg/g, 0.3-20 mg/g, 0.5-10 mg/g, 0.5-15 mg/g, or 0.5-20 mg/g.

When the injectable pharmaceutical composition of the present invention contains peptide (1) as component (a), the composition desirably further contains methionine in view of the stability of the peptide when it is prepared as a cancer vaccine composition. By containing methionine, oxidation of methionine residue contained in peptide (1) can be suppressed when it is prepared as a cancer vaccine composition.

The "methionine" in the present invention is one of the essential amino acids, and is a hydrophobic amino acid comprising a sulfur atom in the side chain. While "methionine" has an optical isomer and includes a D form, an L form and a DL form, any of these can be used without influencing the effect of the invention. Methionine is frequently used as an excipient for pharmaceutical products, and an L form described in the Japanese Pharmacopoeia (the 16th Edition) is preferable. In the injectable pharmaceutical composition of the present invention, the content of methionine relative to the weight of the composition is not particularly defined. The content thereof relative to the weight of the preparation in a liquid form of the present invention is, for example, 1-5 mg/g, 1-10 mg/g, 1-20 mg/g, 1-30 mg/g, 3-10 mg/g, 3-20 mg/g, 3-30 mg/g, 5-10 mg/g, 5-20 mg/g, 5-30 mg/g or the like.

In addition, the injectable pharmaceutical composition of the present invention may appropriately comprise, besides the above-mentioned components, excipients generally used for pharmaceutical formulations such as stabilizer, solubilizing agent, buffering agent, isotonic agent and the like, as long as the effect of the invention is not affected.

The injectable pharmaceutical composition of the present invention can be produced by a method generally used for the production of pharmaceutical products and the like. For example, water for injection is added into a suitable container under an environment maintained at a constant temperature of 5-25° C., and a peptide and an excipient which are weighed in advance are added thereto while gently stirring the mixture. Then, the mixture is finally adjusted to have a desired pH. The mixture is sterilized by filtration and the like, and filled in a container such as a glass vial and the like, which is sealed with a rubber stopper and the like. When a freeze-dried formulation is produced, the obtained formulation in a liquid form of the present invention can be freeze-dried by a method known per se.

While the peptides of the present invention can also be used, each singly, as an antigen peptide for a cancer vaccine, both peptide (1) and peptide (2) may also be contained in a cancer vaccine composition. Since peptide (2) singly binds to HLA by itself and induces CTL, as well as affords effects as helper peptide when used in combination with peptide (1), a cancer vaccine composition containing both peptide (1) and peptide (2) is expected to show a synergistic vaccine effect. When the both peptides are contained in a cancer vaccine composition, a single injectable pharmaceutical composition of the present invention containing the both peptides may be mixed with adjuvant, or two injectable pharmaceutical compositions of the present invention containing each peptide may be mixed with adjuvant to form a mixture of three materials.

The formulation in a liquid form of the present invention, which contains both peptide (1) and peptide (2), can be directly prepared (in a single step) by subjecting the both peptides to the above-mentioned production method, or can also be obtained by subjecting each peptide to the above-mentioned production to prepare individual liquid formulation or suspension formulation and mixing them. In one preferable embodiment, a method including freeze-drying a liquid formulation or a suspension formulation containing peptide (1), and adding a liquid formulation or a suspension formulation containing peptide (2) to dissolve or suspend the freeze-dried formulation containing peptide (1) can be mentioned. Alternatively, two kinds of freeze-dried formulations containing respective peptides are prepared, the freeze-dried formulation containing peptide (2) is redissolved or resuspended in a smaller amount of water than the liquid formulation or suspension formulation before freeze-drying, and the solution or suspension is added to a freeze-dried formulation containing peptide (1) to dissolve or suspend same therein, whereby a liquid preparation or suspension formulation having a higher concentration than that of the liquid formulation or suspension formulation before freeze-drying can be prepared.

While the preparation method of a cancer vaccine using the injectable pharmaceutical composition of the present invention is not particularly limited, for example, a preparation method of a cancer vaccine by mixing with an appropriate adjuvant; a preparation method of a cancer vaccine by mixing with an appropriate adjuvant in advance, and freeze-drying the mixture and the like; a preparation method of a cancer vaccine by mixing the formulation in a liquid form of the present invention with various adjuvants when in use and the like can be mentioned. Examples of the adjuvant include settleability adjuvant, oily adjuvant and the like. The settleability adjuvant is a suspension of an inorganic substance to which the peptides adsorb. Specific examples of the settleability adjuvant include sodium hydroxide, aluminum hydroxide (Alum), calcium phosphate, aluminum phosphate, aluminum potassium sulfate, PEPES, carboxyvinyl polymer and the like. The oily adjuvant is an oil emulsion in which an aqueous solution containing peptide is enveloped in mineral oil to form micelles for emulsification. Specific examples of the oily adjuvant include liquid paraffin, lanolin, Freund's adjuvant (complete Freund's adjuvant, incomplete Freund's adjuvant), Montanide, W/O emulsion (see WO 2006/078059) and the like.

A cancer vaccine prepared using the injectable pharmaceutical composition of the present invention can be used for the prevention or treatment of cancer associated with an increase in the expression level of WT1 gene, for example, hematological cancer such as leukemia, myelodysplastic syndrome, multiple myeloma, malignant lymphoma and the like, and solid tumor such as gastric cancer, colorectal cancer, lung cancer, breast cancer, germ cell cancer, liver cancer, skin cancer, urinary bladder cancer, prostate cancer, uterine cancer, cervical cancer, ovarian cancer, brain tumor and the like.

Since the injectable pharmaceutical composition of the present invention can stably maintain a cancer antigen peptide, which is the active ingredient, various administration forms can be selected. Specifically, oral, transnasal, pulmonary, transdermal, intradermal, subcutaneous, intramuscular, intravenous or intraperitoneal administration and the like can be mentioned, and a cancer vaccine can be prepared by the above-mentioned method according to the object of use. Generally, as an administration route preferable for immunostimulation with a cancer vaccine, parenteral administration is known and, for example, intraperitoneal administration, subcutaneous administration, intradermal administration, intramuscular administration, intravenous administration, as well as transnasal administration, transdermal administration and the like can be mentioned. Of these, administration by injection such as subcutaneous administration, intradermal administration, intraperitoneal administration, intramuscular administration and the like can be preferably mentioned.

EXAMPLES

The present invention is explained in more detail in the following by referring to Examples, Comparative Examples, Experimental Examples and the like, which are not to be construed as limitative.

As a peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) (peptide (2)), a peptide produced by the method described in patent document (WO 2010/123065) was used; as trehalose, "trehalose SG (manufactured by Hayashibara Biochemical Lab)" which is a trehalose hydrate was used; and as D-mannitol, "mannit S (manufactured by Mitsubishi Shoji Foodtech) or D-(−)-Mannitol low in endotoxins (manufactured by Merck)" was used. As tromethamol, "tromethamol (manufactured by Nacalai Tesque)" was used; as histidine, "histidine (manufactured by Nacalai Tesque)" was used; as L-arginine, "L-arginine hydrochloride (manufactured by Nacalai Tesque)" was used; and as meglumine, "meglumine (manufactured by Nacalai Tesque)" was used. As lactic acid, "lactic acid (manufactured by Nacalai Tesque)" was used; as tartaric acid, "L(+)-Tartaric acid, powder (manufactured by Merck)" was used; and as citric acid, "Citric Acid Monohydrate (manufactured by Nacalai Tesque)" was used. As methionine, "L-methionine (manufactured by Kyowa Hakko Bio Co., Ltd.)" was used. As pH adjuster, hydrochloric acid, "1 mol/l-hydrochloric acid (manufactured by Nacalai Tesque)" was used; as sodium hydroxide, "1 mol/l-sodium hydroxide solution (manufactured by Nacalai Tesque)" was used; and as sodium dihydrogen phosphate, "sodium dihydrogen phosphate (manufactured by Nacalai Tesque)" was used. As Montanide, "(Montanide ISA 51 VG (manufactured by SEPPIC)" was used.

[Synthesis of Peptide]
Synthesis of Peptide Represented by the Formula (1) (Peptide (1))
Step 1. Synthesis of H-Cys(Npys)-Arg-Met-Phe-Pro-Asn-Ala-Pro-Tyr-Leu-OH
(Synthesis of C(Npys)RMFPNAPYL)

Using Fmoc-Leu-Alko-resin (Alko is p-alkoxybenzyl alcohol), 282 mg, (manufactured by Watanabe Chemical; 0.71 mmol/g, 0.2 mmol) as a starting material, the peptide chain was assembled by solid phase synthesis according to Fmoc/tBu method. Solid phase synthesis was performed using CS336X peptide synthesizer manufactured by CS Bio, and deprotection of Fmoc group was performed by treatment with a DMF solution of 20% piperidine for 5 min and for 20 min. Coupling of protected amino acid was performed by reaction with a DMF solution of 1.05 mmol of protected amino acid, 1 mmol HBTU and 2 mmol DIPEA for 1 hr. The obtained resin was washed with DMF and ether, and dried under reduced pressure to give Boc-Cys(Npys)-Arg(Pmc)-Met-Phe-Pro-Asn(Trt)-Ala-Pro-Tyr(tBu)-Leu-Alko-resin (630 mg). To this peptide resin was added a mixture (10 ml) of TFA/H$_2$O/TIS=95/2.5/2.5, and the mixture was shaken at room temperature for 2 hr. The resin was filtered off, and the reaction mixture was concentrated under reduced pressure. The reaction mixture was ice-cooled and diethyl ether (50 ml) was added. The resulting precipitate was collected by filtration, washed with ether and dried under reduced pressure to give a crude peptide (217 mg). The obtained crude peptide solution was dissolved in a mixture of 20% aqueous acetic acid (7 ml) and acetonitrile (1 ml) and purified by reversed-phase HPLC.
pump: manufactured by Shimazu; LC-8A
column: YMC ODS-A 3 cm φ×25 cm L, 10 μm
eluate 1: H$_2$O/0.1% TFA
eluate 2: CH$_3$CN/0.1% TFA
flow rate: 20 ml/min
detection: UV 220 nm The crude peptide solution was injected to a column equilibrated with 15% of eluate 2. Thereafter, the concentration of eluate 2 was raised to 37% over 10 min, and thereafter raised at a rate of 0.24% per min. Fractions containing the object product were collected and freeze dried to give H-Cys(Npys)-Arg-Met-Phe-Pro-Asn-Ala-Pro-Tyr-Leu-OH (53 mg).

mass spectrometry: LC-ESI/MS m/z=1366.1 [M+1]+ (Calculated=1366.6)
Step 2. Synthesis of (H-Cys-Tyr-Thr-Trp-Asn-Gln-Met-Asn-Leu-OH) (H-Cys-Arg-Met-Phe-Pro-Asn-Ala-Pro-Tyr-Leu-OH) Disulfide Bond
[Synthesis of Compound Represented by the Formula (1):

(1)
Cys-Arg-Met-Phe-Pro-Asn-Ala-Pro-Tyr-Leu-OH
|
Cys-Tyr-Thr-Trp-Asn-Gln-Met-Asn-Leu-OH wherein the bond between Cys and Cys is a disulfide bond, Leu-OH shows that the C-terminal of Leu is a free carboxyl group, and other bond is a peptide bond.]

H-Cys(Npys)-Arg-Met-Phe-Pro-Asn-Ala-Pro-Tyr-Leu-OH (50 mg) obtained in step 1 and H-Cys-Tyr-Thr-Trp-Asn-Gln-Met-Asn-Leu-OH (i.e., CYTWNQMNL (SEQ ID NO: 4)) (43 mg) synthesized by a known method (e.g., WO 07/063903) were mixed, DMSO (1 mL) was added, and the mixture was stirred at room temperature for 20 min. The reaction mixture was diluted with 0.1% TFA water (5 ml) and purified by reversed-phase HPLC.
pump: manufactured by Shimazu; LC-8A
column: YMC ODS-A 3 cm φ×25 cm L, 10 μm
eluate 1: H₂O/0.1% TFA
eluate 2: CH₃CN/0.1% TFA
flow rate: 20 ml/min
detection: UV 220 nm The reaction solution was injected to a column equilibrated with 25% of eluate 2. Thereafter, the concentration of eluate 2 was raised at a rate of 0.25% per min. Fractions containing the object product were collected, freeze-dried, re-purified by reversed-phase HPLC, and freeze-dried to give (H-Cys-Tyr-Thr-Trp-Asn-Gln-Met-Asn-Leu-OH) (H-Cys-Arg-Met-Phe-Pro-Asn-Ala-Pro-Tyr-Leu-OH) disulfide bond (i.e., peptide represented by the formula (1) (peptide (1)) (21 mg).

mass spectrometry: LC-ESI/MS m/z=1191.8 [M+2]2+ (Calculated=1191.9)

(1)

wherein the bond between Cys and Cys is a disulfide bond, Leu-OH shows that the C-terminal of Leu is a free carboxyl group, and other bond is a peptide bond.

[Preparation of Liquid Formulation or Suspension Formulation]

Example 1

The above-mentioned peptide (1) as a peptide (component (a)), and trehalose as component (b) were dissolved in water for injection in the amounts described in Table 1, and the mixture was adjusted to pH 1 with hydrochloric acid and/or sodium hydroxide as a pH adjuster (component (c)). After filtration through a 0.2 μm sterilization filter, and the mixture was filled in a glass vial by 1 mL, and tightly sealed with a butyl rubber stopper, whereby the liquid formulation of Example 1 was obtained.

Examples 2-10

In the same manner as in Example 1, peptide (1), trehalose, a pH adjuster (hydrochloric acid and/or sodium hydroxide), and water for injection were prepared in the amounts described in Table 1 or 2, filled in a vial, and tightly sealed with a butyl rubber stopper, whereby the liquid formulations of Examples 2, 3, 5-8 and 10 were obtained.

In the same manner as in Example 1, peptide (1), trehalose, a pH adjuster (hydrochloric acid and/or sodium hydroxide), and water for injection were prepared in the amounts described in Table 1 or 2, filled in a vial, and tightly sealed with a butyl rubber stopper, whereby the liquid formulations of Examples 4 and 9 were obtained.

TABLE 1

| Component | Example 1 | Example 2 | Example 3 | Example 4 | Example 5 |
|---|---|---|---|---|---|
| peptide (1) (mg) | 10 | 10 | 10 | 10 | 10 |
| trehalose (mg) | 10 | 10 | 10 | 10 | 10 |
| hydrochloric acid | | | q.s. | | |
| sodium hydroxide | | | q.s. | | |
| water for injection | | | q.s. | | |
| pH | 1 | 1.5 | 2 | 2.5 | 3 |
| total amount | | | 2 g | | |

TABLE 2

| Component | Example 6 | Example 7 | Example 8 | Example 9 | Example 10 |
|---|---|---|---|---|---|
| peptide (1) (mg) | 10 | 10 | 10 | 10 | 10 |
| trehalose (mg) | 20 | 20 | 20 | 20 | 20 |
| hydrochloric acid | | | q.s. | | |
| sodium hydroxide | | | q.s. | | |
| water for injection | | | q.s. | | |
| pH | 1 | 1.5 | 2 | 2.5 | 3 |
| total amount | | | 2 g | | |

Examples 11-19

In the same manner as in Example 1, the peptide shown in SEQ ID NO: 1 (WAPVLDFAPPGASAYGSL) (hereinafter peptide (2)) as component (a), trehalose, a pH adjuster (hydrochloric acid and/or sodium hydroxide), and water for injection were prepared in the amounts described in Table 3 or 4, filled in a vial, and tightly sealed with a butyl rubber stopper, whereby the liquid formulations of Examples 12, 15 and 18 were obtained.

In the same manner as in Example 1, the peptide shown in SEQ ID NO: 1 (WAPVLDFAPPGASAYGSL) (hereinafter peptide (2)) as component (a), trehalose, a pH adjuster (hydrochloric acid and/or sodium hydroxide), and water for injection are prepared in the amounts described in Table 3 or 4, filled in a vial, and tightly sealed with a butyl rubber stopper, whereby the liquid formulations of Examples 11, 13, 14, 16, 17 and 19 are obtained.

TABLE 3

| component | Example 11 | Example 12 | Example 13 | Example 14 | Example 15 |
|---|---|---|---|---|---|
| peptide (2) (mg) | 2 | 2 | 2 | 2 | 2 |
| trehalose (mg) | 10 | 10 | 10 | 10 | 10 |
| hydrochloric acid | | | q.s. | | |
| sodium hydroxide | | | q.s. | | |
| water for injection | | | q.s. | | |
| pH | 2 | 3 | 4 | 5 | 6 |
| total amount | | | 2 g | | |

TABLE 4

| component | Example 16 | Example 17 | Example 18 | Example 19 |
|---|---|---|---|---|
| peptide (2) (mg) | 2 | 2 | 2 | 2 |
| trehalose (mg) | 10 | 10 | 10 | 10 |
| hydrochloric acid | | | q.s. | |
| sodium hydroxide | | | q.s. | |
| water for injection | | | q.s. | |
| pH | 7 | 8 | 9 | 10 |
| total amount | | | 2 g | |

Examples 20-24

In the same manner as in Example 1, peptide (1), trehalose, D-mannitol, water for injection, a pH adjuster (hydrochloric acid and/or sodium hydroxide) were prepared in the amounts described in Table 5, filled in a vial, and tightly sealed with a butyl rubber stopper, whereby the liquid formulations of Examples 20-24 were obtained.

TABLE 5

| component | Example 20 | Example 21 | Example 22 | Example 23 | Example 24 |
|---|---|---|---|---|---|
| peptide (1) (mg) | 10 | 20 | 20 | 20 | 20 |
| trehalose (mg) | 20 | 20 | 20 | 20 | 20 |
| D-mannitol (mg) | 10 | 10 | 10 | 10 | 10 |
| hydrochloric acid | | | q.s. | | |
| water for injection | | | q.s. | | |
| pH | 1 | 1.5 | 2 | 2.5 | 3 |
| total amount | | | 2 g | | |

Example 25

Peptide (1) and trehalose prepared in the amounts described in Table 6 were added to a suitable amount of water for injection, and the mixture was dispersed by a stirring machine, after which the pH was adjusted to 4 with hydrochloric acid and/or sodium hydroxide as a pH adjuster to give the suspension formulation of Example 25.

Examples 26-29

In the same manner as in Example 25, peptide (1) and trehalose prepared in the amounts described in Table 6 were added to a suitable amount of water for injection, and the pH adjuster described in Table 6 were used and adjusted to the pH of Table 6 to give the suspension formulations of Examples 26-29.

TABLE 6

| component | Example 25 | Example 26 | Example 27 | Example 28 | Example 29 |
|---|---|---|---|---|---|
| peptide (1) (mg) | 10 | 10 | 10 | 10 | 10 |
| trehalose (mg) | 10 | 10 | 10 | 10 | 10 |
| hydrochloric acid | | | q.s. | | |
| sodium hydroxide | | | q.s. | | |
| water for injection | | | q.s. | | |
| pH | 4 | 6 | 7 | 8 | 10 |
| total amount | | | 2 g | | |

Example 30

Peptide (2) as the peptide (component (a)), trehalose (component (b)), tromethamol as the pH adjuster (component (c)) were dissolved in water for injection to the amounts described in Table 7. After filtration through a 0.2 μm sterilization filter, and the mixture was filled in a glass vial by 1 mL, and tightly sealed with a butyl rubber stopper, whereby the liquid formulation of Example 30 was obtained.

Examples 31-34

In the same manner as in Example 30, peptide (2), trehalose, a pH adjuster, and water for injection were prepared in the amounts described in Table 7, filled in a vial, and tightly sealed with a butyl rubber stopper, whereby the liquid formulations of Examples 31-34 were obtained.

TABLE 7

| component | Example 30 | Example 31 | Example 32 | Example 33 | Example 34 |
|---|---|---|---|---|---|
| peptide (2) (mg) | 20 | 20 | 20 | 20 | 20 |
| trehalose (mg) | 20 | 20 | 20 | 20 | 20 |
| tromethamol (mg) | 20 | — | — | — | — |
| histidine (mg) | — | 40 | — | — | — |
| L-arginine (mg) | — | — | 20 | — | — |
| meglumine (mg) | — | — | — | 20 | — |
| disodium hydrogen-phosphate (mg) | — | — | — | — | 20 |
| hydrochloric acid | | | q.s. | | |
| water for injection | | | q.s. | | |
| pH | 7 | 7 | 7 | 7 | 7 |
| total amount | | | 2 g | | |

Examples 35-37

In the same manner as in Example 1, peptide (2), trehalose, solubilizing agents (citric acid, lactic acid, tartaric acid), a pH adjuster (hydrochloric acid), and water for injection were prepared in the amounts described in Table 8, filled in a vial, and tightly sealed with a butyl rubber stopper, whereby the liquid formulations of Examples 35-37 were obtained.

TABLE 8

| component | Example 35 | Example 36 | Example 37 |
|---|---|---|---|
| peptide (2) (mg) | 100 | 100 | 100 |
| trehalose (mg) | 500 | 500 | 500 |
| citric acid (mg) | 55 | — | — |
| lactic acid (mg) | — | 50 | — |
| tartaric acid (mg) | — | — | 50 |
| hydrochloric acid | | q.s. | |
| water for injection | | q.s. | |
| pH | 2.6 | 2.8 | 2.5 |
| total amount | | 10 g | |

Examples 38-43

In the same manner as in Example 1, peptide (2), trehalose, a solubilizing agent (tartaric acid), a pH adjuster (hydrochloric acid), and water for injection were prepared in the amounts described in Table 9 or 10, filled in a vial, and tightly sealed with a butyl rubber stopper, whereby the liquid formulations of Examples 38-43 were obtained.

TABLE 9

| component | Example 38 | Example 39 | Example 40 |
|---|---|---|---|
| peptide (2) (mg) | 150 | 150 | 200 |
| trehalose (mg) | 200 | 800 | 200 |
| tartaric acid (mg) | 30 | 50 | 30 |
| hydrochloric acid | | q.s. | |
| water for injection | | q.s. | |
| pH | 2.5 | 2.6 | 2.5 |
| total amount | | 10 g | 20 g |

TABLE 10

| component | Example 41 | Example 42 | Example 43 |
|---|---|---|---|
| peptide (2) (mg) | 200 | 113 | 113 |
| trehalose (mg) | 800 | 225 | 300 |
| tartaric acid (mg) | 50 | 22.5 | 37.5 |
| hydrochloric acid | | q.s. | |
| water for injection | | q.s. | |
| pH | 2.5 | 2.5 | 2.5 |
| total amount | 20 g | 15 g | |

Examples 44-47

In the same manner as in Example 1, peptide (2), trehalose, a solubilizing agent (tartaric acid), a pH adjuster (hydrochloric acid), and water for injection were prepared in the amounts described in Table 11, filled in a vial, and tightly sealed with a butyl rubber stopper, whereby the liquid formulations of Examples 44-47 were obtained.

TABLE 11

| component | Example 44 | Example 45 | Example 46 | Example 47 |
|---|---|---|---|---|
| peptide (2) (mg) | 150 | 151 | 151 | 151 |
| trehalose (mg) | 113 | 113 | 113 | 113 |
| tartaric acid (mg) | — | 7.5 | 22.5 | 37.5 |
| hydrochloric acid | | q.s. | | |
| water for injection | | q.s. | | |
| pH | 2.5 | 2.6 | 2.5 | 2.5 |
| total amount | | 15 g | | |

Examples 48-50

In the same manner as in Example 1, peptide (1), trehalose, D-mannitol, water for injection, and a pH adjuster (hydrochloric acid) were prepared in the amounts described in Table 12, filled in a vial, and tightly sealed with a butyl rubber stopper, whereby the liquid formulations of Examples 48-50 were obtained.

TABLE 12

| component | Example 48 | Example 49 | Example 50 |
|---|---|---|---|
| peptide (1) (mg) | 91 | 92 | 92 |
| trehalose (mg) | 46 | 138 | 46 |
| D-mannitol (mg) | 46 | 92 | 138 |
| hydrochloric acid | | q.s. | |
| water for injection | | q.s. | |
| pH | 2.3 | 2.3 | 2.3 |
| total amount | 9.1 g | 9.2 g | |

Examples 51-54

In the same manner as in Example 1, peptide (1), trehalose, D-mannitol, methionine, water for injection, and a pH adjuster (hydrochloric acid) were prepared in the amounts described in Table 13, filled in a vial, and tightly sealed with a butyl rubber stopper, whereby the liquid formulation of Example 52 was obtained.

In the same manner as in Example 1, peptide (1), trehalose, D-mannitol, methionine, water for injection, and a pH adjuster (hydrochloric acid) are prepared in the amounts described in Table 13, filled in a vial, and tightly sealed with a butyl rubber stopper, whereby the liquid formulations of Examples 51, 53 and 54 are obtained.

TABLE 13

| component | Example 51 | Example 52 | Example 53 | Example 54 |
|---|---|---|---|---|
| peptide (1) (mg) | 20 | 20 | 20 | 20 |
| trehalose (mg) | 10 | 20 | 10 | 20 |
| D-mannitol (mg) | 10 | 10 | 10 | 10 |
| L-methionine (mg) | 15 | 15 | 15 | 15 |
| hydrochloric acid | | q.s. | | |
| water for injection | | q.s. | | |
| pH | 2.5 | 2.5 | 3 | 3 |
| total amount | | 2 g | | |

Examples 55-58

In the same manner as in Example 1, peptide (2), trehalose, tartaric acid, water for injection, and a pH adjuster (hydrochloric acid) are prepared in the amounts described in Table 14, filled in a vial, and tightly sealed with a butyl rubber stopper, whereby the liquid formulations of Examples 55 and 56 were obtained.

In the same manner as in Example 1, peptide (2), trehalose, tartaric acid, water for injection, and a pH adjuster (hydrochloric acid) are prepared in the amounts described in Table 14, filled in a vial, and tightly sealed with a butyl rubber stopper, whereby the liquid formulations of Examples 57 and 58 are obtained.

TABLE 14

| component | Example 55 | Example 56 | Example 57 | Example 58 |
|---|---|---|---|---|
| peptide (2) (mg) | 18 | 18 | 18 | 18 |
| trehalose (mg) | 36 | 24 | 36 | 24 |
| tartaric acid (mg) | 3.6 | 3.6 | 3.6 | 3.6 |
| hydrochloric acid | | q.s. | | |
| water for injection | | q.s. | | |
| pH | 2.5 | 2.5 | 3 | 3 |
| total amount | | 2.4 g | | |

Examples 59-66

In the same manner as in Example 1, peptide (1), peptide (2), trehalose, D-mannitol, L-methionine, tartaric acid, water for injection, and a pH adjuster (hydrochloric acid) are prepared in the amounts described in Table 15 or 16, filled in a vial, and tightly sealed with a butyl rubber stopper, whereby the liquid formulations of Examples 59-66 are obtained.

TABLE 15

| component | Example 59 | Example 60 | Example 61 | Example 62 |
|---|---|---|---|---|
| peptide (1) (mg) | 40 | 40 | 40 | 40 |
| peptide (2) (mg) | 30 | 30 | 30 | 30 |
| trehalose (mg) | 30 | 40 | 45 | 50 |
| D-mannitol (mg) | 10 | 10 | 10 | 10 |
| L-methionine (mg) | 30 | 30 | 30 | 30 |
| tartaric acid (mg) | 6 | 6 | 6 | 6 |
| hydrochloric acid | | q.s. | | |
| water for injection | | q.s. | | |
| pH | 2.5 | 2.5 | 2.5 | 2.5 |
| total amount | | 4 g | | |

TABLE 16

| component | Example 63 | Example 64 | Example 65 | Example 66 |
|---|---|---|---|---|
| peptide (1) (mg) | 40 | 40 | 40 | 40 |
| peptide (2) (mg) | 30 | 30 | 30 | 30 |
| trehalose (mg) | 30 | 40 | 45 | 50 |
| D-mannitol (mg) | 10 | 10 | 10 | 10 |
| L-methionine (mg) | 30 | 30 | 30 | 30 |
| tartaric acid (mg) | 6 | 6 | 6 | 6 |
| hydrochloric acid | | | q.s. | |
| water for injection | | | q.s. | |
| pH | 3 | 3 | 3 | 3 |
| total amount | | | 4 g | |

[Preparation of Freeze-Dried Formulation]

Examples 1A-66A

The liquid formulations or suspension formulations produced in Examples 1, 4, 6, 9, 11, 13, 14, 16, 17, 19, 20, 51, 53, 54 and 57-66 are filled in glass vials, placed in a freeze dryer and freeze-dried to give the freeze-dried formulations of Examples 1A, 4A, 6A, 9A, 11A, 13A, 14A, 16A, 17A, 19A, 20A, 51A, 53A, 54A and 57A-66A. The freeze-drying is performed under the conditions including freezing a liquid formulation or a suspension formulation at near −40° C., reducing the pressure in the freeze dryer to vacuum, simultaneously increasing the temperature in the freeze dryer to near −20° C. and drying for about 20 hr, and increasing the temperature in the freeze dryer to near 30° C. and drying for about 12 hr.

The liquid formulations produced in Examples 2, 3, 5, 7, 8, 10, 12, 15, 18, 21-50, 52, 55 and 56 were filled in glass vials, placed in a freeze dryer and freeze-dried to give the freeze-dried formulations of Examples 2A, 3A, 5A, 7A, 8A, 10A, 12A, 15A, 18A, 21A-50A, 52A, 55A and 56A. The freeze-drying was performed under the conditions including freezing a liquid formulation or a suspension formulation at near −40° C., reducing the pressure in the freeze dryer to vacuum, simultaneously increasing the temperature in the freeze dryer to near −20° C. and drying for about 20 hr, and increasing the temperature in the freeze dryer to near 30° C. and drying for about 12 hr.

[Experimental Example 1] Evaluation of Stability of Liquid and Suspension Formulations The liquid formulations of Example 2, 3, 5, 7, 8, 10, 12, 15, 18, 21-26, 30-34 and 52 were stored at 25° C. for 1 week, and the purity was evaluated. The purity was measured by a reversed-phase high performance liquid chromatography method (detection wavelength: 220 nm) using C18 reversed-phase column (2.1 mm×150 mm, 1.7 μm or 4.6 mm×150 mm, 5 μm) and pure water, acetonitrile, trifluoroacetic acid as mobile phase. Using the peak area measured by this method, the relative purity (vs initial value) based on the purity of peptide and the purity before storage as 100% was calculated by the following formula.

purity of peptide (%)=peak area of peptide/total peak area containing related substance×100 relative purity(vs. initial value)(%)=purity of peptide on stored sample/purity of peptide before storage×100

The results are shown in Table 17. Every formulation showed not less than 80% at 25° C., 1 week, and a stable formulation could be obtained.

TABLE 17

| | purity (vs initial value) (%) | |
|---|---|---|
| | before storage | 25° C., 1 week |
| Example 2 | 100 | 94 |
| Example 3 | 100 | 99 |
| Example 5 | 100 | 99 |
| Example 7 | 100 | 94 |
| Example 8 | 100 | 98 |
| Example 10 | 100 | 100 |
| Example 12 | 100 | 98 |
| Example 15 | 100 | 100 |
| Example 18 | 100 | 100 |
| Example 21 | 100 | 94 |
| Example 22 | 100 | 98 |
| Example 23 | 100 | 99 |
| Example 24 | 100 | 100 |
| Example 25 | 100 | 99 |
| Example 26 | 100 | 94 |
| Example 30 | 100 | 100 |
| Example 31 | 100 | 100 |
| Example 32 | 100 | 100 |
| Example 33 | 100 | 100 |
| Example 34 | 100 | 100 |
| Example 52 | 100 | 99 |

[Experimental Example 2] Evaluation of Stability of Freeze-Dried Formulation

The freeze-dried formulations of Examples 5A, 10A, 12A, 15A, 18A, 23A-26A, 30A-43A, 48A-50A, 52A, 55A and 56A were preserved at 60° C. for 2 weeks, water for injection was added to convert to liquid formulations, and the purity was evaluated. The purity was measured and calculated in the same manner as in Experimental Example 1.

The results are shown in Table 18. Every formulation showed not less than 80% at 60° C., 2 weeks, and a stable formulation could be obtained.

TABLE 18

| | purity (vs. initial value) (%) | |
|---|---|---|
| | before storage | 60° C., 2 week |
| Example 5A | 100 | 95 |
| Example 10A | 100 | 95 |
| Example 12A | 100 | 82 |
| Example 15A | 100 | 100 |
| Example 18A | 100 | 100 |
| Example 23A | 100 | 92 |
| Example 24A | 100 | 99 |
| Example 25A | 100 | 98 |
| Example 26A | 100 | 98 |
| Example 30A | 100 | 99 |
| Example 31A | 100 | 100 |
| Example 32A | 100 | 100 |
| Example 33A | 100 | 99 |
| Example 34A | 100 | 99 |
| Example 35A | 100 | 91 |
| Example 36A | 100 | 92 |
| Example 37A | 100 | 97 |
| Example 38A | 100 | 97 |
| Example 39A | 100 | 98 |
| Example 40A | 100 | 97 |
| Example 41A | 100 | 99 |
| Example 42A | 100 | 97 |
| Example 43A | 100 | 97 |
| Example 48A | 100 | 96 |
| Example 49A | 100 | 94 |
| Example 50A | 100 | 94 |
| Example 52A | 100 | 96 |

TABLE 18-continued

| | purity (vs. initial value) (%) | |
|---|---|---|
| | before storage | 60° C., 2 week |
| Example 55A | 100 | 97 |
| Example 56A | 100 | 96 |

[Experimental Example 3] Evaluation of Resolubility of Freeze-Dried Formulation

The freeze-dried formulations of Examples 44A-47A were stored at 40° C. for 1 month, and the dissolution property when water for injection was added to reconstitute water was confirmed by visual observation. The results are shown in Table 19. The results of Table 19 suggest that addition of tartaric acid as a solubilizing agent in advance improves resolubility.

TABLE 19

| | resolubility |
|---|---|
| Example 44A | Shaking by hand for 5 min after addition of water for injection did not cause dissolution. Dissolved after stirring by touch mixer for 3 min and sonication for several seconds. |
| Example 45A | Shaking by hand for 2 min after addition of water for injection did not cause dissolution. Dissolved after stirring by touch mixer for 3 min. |
| Example 46A | Rapidly dissolved after addition of water for injection. |
| Example 47A | Rapidly dissolved after addition of water for injection. |

[Experimental Example 4] Confirmation of Specific CTL-Inducing Activity

The liquid formulation of Example 67 containing peptide (1), trehalose, D-mannitol, methionine, water for injection, a pH adjuster (hydrochloric acid) at the same composition ratio as in Example 51 and having a pH adjusted to 2.7 was obtained. The liquid formulation of Example 67 was filled in a vial by 2 mL, placed in a freeze dryer and freeze-dried to give the freeze-dried formulation of Example 67A. The freeze-dried formulation of Example 67A containing peptide (1) and the freeze-dried formulation of Example 55A containing peptide (2) were mixed with adjuvant to give a cancer vaccine composition. In addition, the stability of the freeze-dried formulation of Example 67A was evaluated in the same manner as in Experimental Example 2. As a result, the relative purity (vs. initial value) after storage at 25° C. for 3 months was 100%, and a stable formulation could be obtained.

1) Preparation of Cancer Vaccine Composition

The freeze-dried formulation of Example 55A containing peptide (2) was reconstituted in 1.2 mL of water for injection. The reconstituted solution was collected by 1 mL, added to and redissolved in the freeze-dried formulation of Example 67A containing peptide (1) to give the liquid formulation of Example 68. The liquid formulation (0.9 mL) was mixed with Montanide (0.9 ml) as an adjuvant and the mixture was emulsified to give the cancer vaccine composition of Example 67.

2) CTL-Inducing Activity Evaluation

The CTL-inducibility of the above-mentioned cancer vaccine composition was evaluated by an in vivo CTL-inducing test using HLA-A*02:01 transgenic mouse and HLA-A*24:02 transgenic mouse.

HLA-A*02:01 transgenic mouse, which is defective in mouse MHC, express chimera HLA of human MHC HLA-A*02:01 and mouse MHC H-2D$^b$ as well as HLA-DRB1*01:01. Using this mouse, a peptide capable of inducing CTL in HLA-A*02 positive human can be selected (Eur J Immunol. 2004; 34:3060-9). On the other hand, HLA-A*24:02 transgenic mouse (C57BL/6CrHLA-A2402/K$^b$) is a mouse that expresses chimera HLA of HLA-A*24:02, which is human MHC, and H-2K$^b$, which is mouse MHC. Using this mouse, a peptide capable of inducing CTL in HLA-A*24 positive human can be selected (Int J Cancer. 2002; 100:565-70).

The above-mentioned cancer vaccine composition was intradermally administered to two sites in the tail base of mouse at 50 μL/site. For evaluation of the peptide specific T cell-induction of the cancer vaccine composition, IFNγ ELISPOT assay kit was used. At one week after the administration, the mouse was euthanized with $CO_2$ gas, the spleen was isolated, and splenocytes were prepared. ELISPOT plate was treated with an anti-mouse IFNγ antibody on the previous day of splenocyte preparation, and blocked with RPMI1640 medium containing 10% FBS on the day of splenocyte preparation. The prepared splenocytes derived from HLA-A*02:01 transgenic mouse were seeded at 1.25×10$^5$ cells/well, and the prepared splenocytes derived from HLA-A*24:02 transgenic mouse were seeded at 5×10$^5$ cells/well, each in the blocked ELISPOT plate. Peptide (SEQ ID NO: 3, 5) was dissolved in DMSO at 40 mg/mL, and further diluted to 40 μg/mL with RPMI 1640 medium containing 10% FBS. The diluted peptide (SEQ ID NO: 3) was added to the HLA-A*02:01 transgenic mouse-derived splenocytes at a final concentration of 10 μg/mL. In addition, the diluted peptide (SEQ ID NO: 5) was added to the HLA-A*24:02 transgenic mouse-derived splenocytes at a final concentration of 10 μg/mL. Thereafter, the cells were cultured for 18-20 hr at 37° C., 5% $CO_2$ to restimulate with peptide in vitro. After culture, the supernatant was removed, and the ELISPOT plate was allowed to develop color according to the attached protocol. The number of spots that developed color was measured by ImmunoSpot Analyzer (manufactured by C.T.L.).

Figure 1:
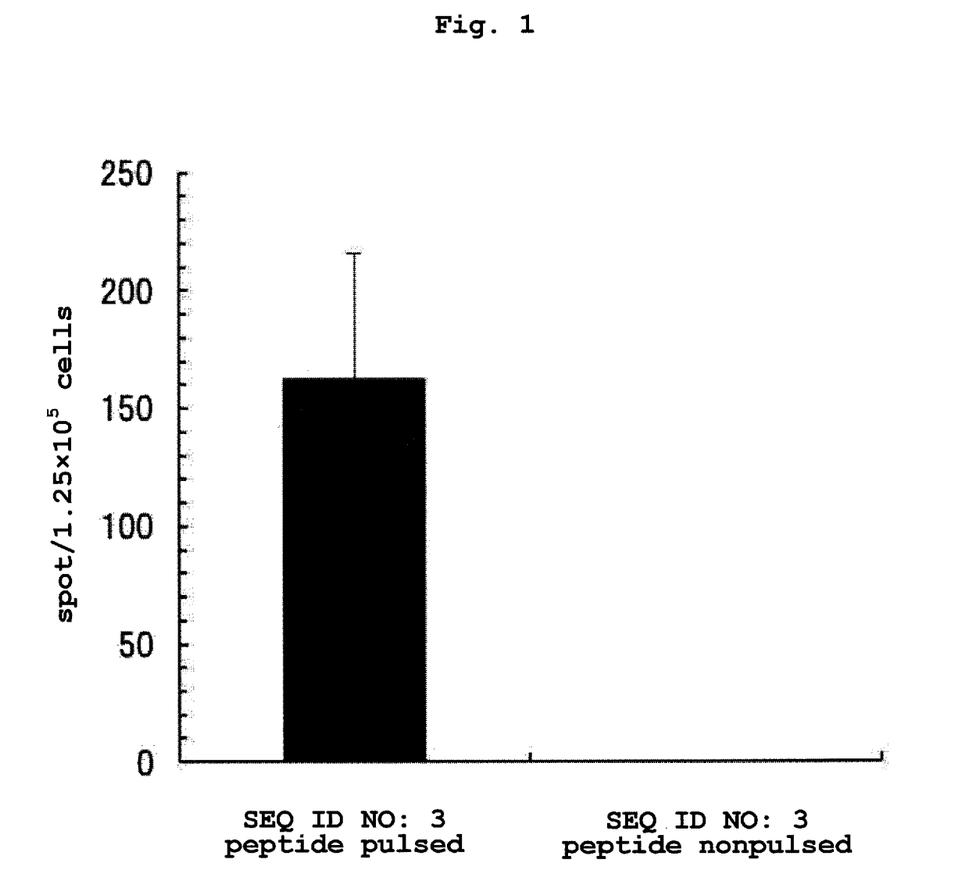
Figure 2:
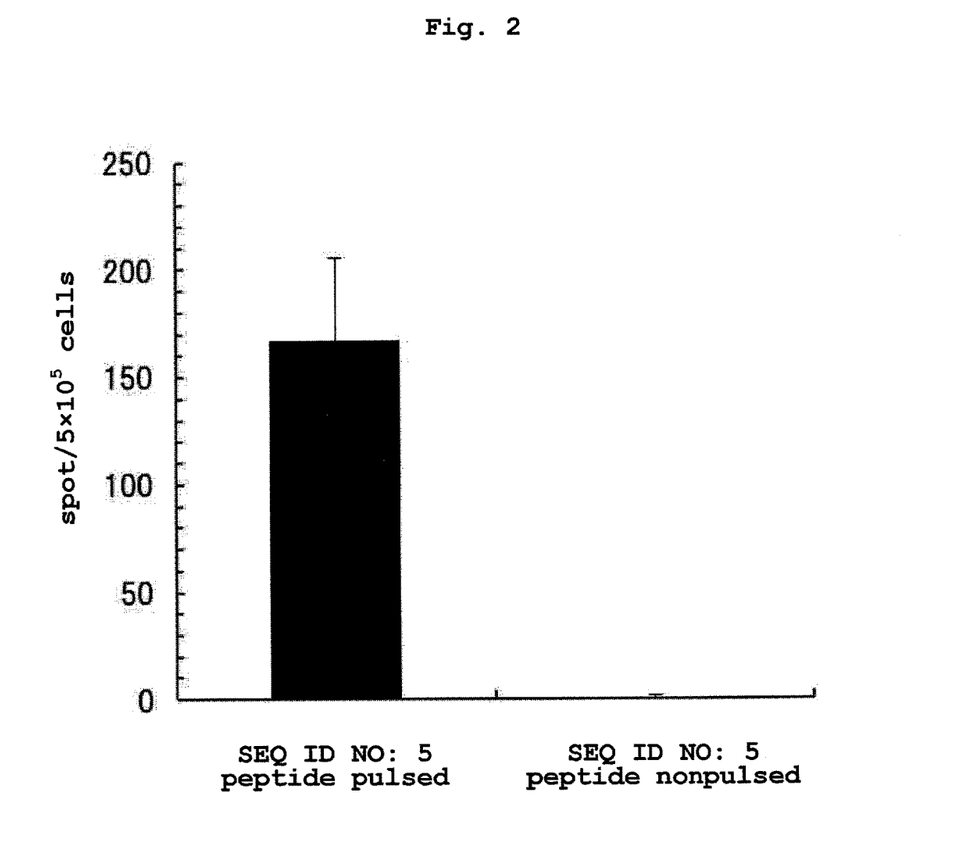

The results of IFNγ ELISPOT assay using HLA-A*02:01 transgenic mouse are shown in FIG. 1, and the results of IFNγ ELISPOT assay using HLA-A*24:02 transgenic mouse are shown in FIG. 2.

In FIGS. 1 and 2, the vertical axis shows the number of cells that reacted in the seeded cells, and the horizontal axis shows peptide pulsed in vitro. In FIG. 1, the black bar shows the results of culture of HLA-A*02:01 transgenic mouse-derived splenocytes by pulsing the peptide shown in SEQ ID NO: 3, and the white bar shows the results of culture without pulsing. That is, a difference in the values of the black bar and the white bar shows the number of peptide-specific CTL, and it was shown that the administration of the above-mentioned cancer vaccine composition induced CTL specific to the peptide shown in SEQ ID NO: 3 in the body of the mouse. In FIG. 1, the white bar does not show a value. This means absence of reaction of splenocytes of HLA-A*02:01 transgenic mouse when the object peptide was not pulsed. As a result of this test, production of IFNγ specific to the peptide shown in SEQ ID NO: 3 was confirmed in the splenocytes derived from HLA-A*02:01 transgenic mouse.

In FIG. 2, moreover, the black bar shows the results of culture of HLA-A*24:02 transgenic mouse-derived splenocytes by pulsing the peptide shown in SEQ ID NO: 5, and the white bar shows the results of culture without pulsing. That is, a difference in the values of the black bar and the white bar shows the number of peptide-reactive cells, and it was shown that the administration of the above-mentioned cancer vaccine composition induced CTL specific to the peptide shown in SEQ ID NO: 5 in the body of the mouse. In FIG. 2, the white bar does not show a value. This means absence of reaction of splenocytes of HLA-A*24:02 transgenic mouse when the object peptide was not pulsed. As a result of this test, production of IFNγ specific to the peptide shown in SEQ ID NO: 5 was confirmed in the splenocytes derived from HLA-A*24:02 transgenic mouse.

Therefrom it was clarified that the above-mentioned cancer vaccine composition can induce CTL specific to the peptides shown in SEQ ID NO: 3 and SEQ ID NO: 5 in vivo. Therefore, it is suggested that a formulation prepared from a formulation wherein peptide including peptide (1) is stable and a formulation wherein peptide including peptide (2) is stable can be used as a cancer vaccine.

INDUSTRIAL APPLICABILITY

According to the present invention, a suspension formulation containing WT1 protein-derived cancer antigen peptide and showing good suspensibility, and a freeze-dried formulation obtained by freeze-drying the suspension formulation and having high stability can be provided, and the peptide can be used as a cancer vaccine.

This application is based on a patent application No. 2014-197667 filed in Japan (filing date: Sep. 27, 2014), the contents of which are incorporated in full herein.

The invention claimed is:

1. An injectable pharmaceutical composition comprising the following components:
   (a) one or more kinds of peptides selected from the group consisting of:
      (i) the peptide represented by the formula (1):

Cys-Arg-Met-Phe-Pro-Asn-Ala-Pro-Tyr-Leu-OH (1)
   |
   Cys-Tyr-Thr-Trp-Asn-Gln-Met-Asn-Leu-OH wherein the bond between Cys and Cys is a disulfide bond, Leu-OH shows that the C-terminal of Leu is a free carboxyl group, and other amino acids in formula (I) are linked by peptide bonds,
      (ii) the peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and
      (iii) salts thereof,
   (b) trehalose or trehalose hydrate, and
   (c) a pH adjuster.

2. The composition according to claim 1, wherein the component (a) is one or more kinds of peptides selected from the group consisting of (i) the peptide represented by the formula (1) and (ii) a salt thereof.

3. The composition according to claim 2, further comprising mannitol.

4. The composition according to claim 3, wherein the mannitol is D-mannitol.

5. The composition according to claim 2, further comprising methionine.

6. The composition according to claim 2, which has a pH of 1-3.

7. The composition according to claim 1, wherein the component (a) is one or more kinds of peptides selected from the group consisting of (i) the peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and (ii) a salt thereof.

8. The composition according to claim 7, further comprising a solubilizing agent.

9. The composition according to claim 8, wherein the solubilizing agent is tartaric acid.

10. The composition according to claim 8, which has a pH of 2-3.

11. The composition according to claim 7, which has a pH of 5-10.

12. The composition according to claim 1, wherein the pH adjuster is hydrochloric acid and/or sodium hydroxide.

13. The composition according to claim 7, wherein the acid used as the pH adjuster is a weak acid.

14. The composition according to claim 1, wherein the component (a) comprises
   one or more kinds of peptides selected from the group consisting of (i) the peptide represented by the formula (1) and (ii) a salt thereof, and
   one or more kinds of peptides selected from the group consisting of (iii) the peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and (iv) a salt thereof.

15. The composition according to claim 14, further comprising mannitol.

16. The composition according to claim 14, further comprising methionine.

17. The composition according to claim 14, further comprising a solubilizing agent.

18. The composition according to claim 14, which has a pH of 2-3.

19. The composition according to claim 1, which is a liquid formulation, a suspension formulation, or a freeze-dried formulation.

20. The composition according to claim 14, which is produced by adding an injectable pharmaceutical composition comprising the following components:
   (a) one or more kinds of peptides selected from the group consisting of:
      (i) the peptide consisting of the amino acid sequence shown by Trp-Ala-Pro-Val-Leu-Asp-Phe-Ala-Pro-Pro-Gly-Ala-Ser-Ala-Tyr-Gly-Ser-Leu (SEQ ID NO: 1) and
      (ii) a salt thereof,
   (b) trehalose or trehalose hydrate, and
   (c) a pH adjuster, which is in the form of a liquid formulation, to an injectable pharmaceutical composition comprising the following components:

(a') one or more kinds of peptides selected from the group consisting of
(iii) the peptide represented by the formula (1):

(1)

wherein the bond between Cys and Cys is a disulfide bond, Leu-OH shows that the C-terminal of Leu is a free carboxyl group, and other amino acids in formula (I) are linked by peptide bonds, and
(iv) a salt thereof,
(b') trehalose or trehalose hydrate, and
(c') a pH adjuster,
which is in the form of a freeze-dried formulation.

21. The composition according to claim 20, which is a liquid formulation or a suspension formulation.

22. A cancer vaccine composition comprising a composition according to claim 2.

* * * * *

SEQUENCE LISTING

```
<160> NUMBER OF SEQ ID NOS: 6

<210> SEQ ID NO 1
<211> LENGTH: 18
<212> TYPE: PRT
<213> ORGANISM: Homo sapiens
<220> FEATURE:
<223> OTHER INFORMATION: peptide

<400> SEQUENCE: 1

Trp Ala Pro Val Leu Asp Phe Ala Pro Pro Gly Ala Ser Ala Tyr Gly
1               5                   10                  15

Ser Leu

<210> SEQ ID NO 2
<211> LENGTH: 449
<212> TYPE: PRT
<213> ORGANISM: Homo sapiens

<400> SEQUENCE: 2

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190
```

-continued

```
Tyr Ser Val Pro Pro Val Tyr Gly Cys His Thr Pro Thr Asp Ser
        195                 200                 205
Cys Thr Gly Ser Gln Ala Leu Leu Arg Thr Pro Tyr Ser Ser Asp
    210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
                245                 250                 255
Ser Val Lys Trp Thr Glu Gly Gln Ser Asn His Ser Thr Gly Tyr Glu
                260                 265                 270
Ser Asp Asn His Thr Thr Pro Ile Leu Cys Gly Ala Gln Tyr Arg Ile
                275                 280                 285
His Thr His Gly Val Phe Arg Gly Ile Gln Asp Val Arg Arg Val Pro
            290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
                355                 360                 365
Gln Leu Lys Arg His Gln Arg Arg His Thr Gly Val Lys Pro Phe Gln
            370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp Pro Ser Cys Gln Lys Lys Phe Ala Arg Ser Asp Glu Leu Val
                420                 425                 430
Arg His His Asn Met His Gln Arg Asn Met Thr Lys Leu Gln Leu Ala
            435                 440                 445
Leu

<210> SEQ ID NO 3
<211> LENGTH: 9
<212> TYPE: PRT
<213> ORGANISM: Homo sapiens
<220> FEATURE:
<223> OTHER INFORMATION: peptide

<400> SEQUENCE: 3

Arg Met Phe Pro Asn Ala Pro Tyr Leu
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

Cys Arg Met Phe Pro Asn Ala Pro Tyr Leu
1               5                   10

<210> SEQ ID NO 5
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Cys Tyr Thr Trp Asn Gln Met Asn Leu
1               5

<210> SEQ ID NO 6
<211> LENGTH: 9
<212> TYPE: PRT
<213> ORGANISM: Homo sapiens
<220> FEATURE:
<223> OTHER INFORMATION: peptide

<400> SEQUENCE: 6

Cys Met Thr Trp Asn Gln Met Asn Leu
1               5
```